United States Patent [19]

Kennis et al.

[11] Patent Number: 5,015,740

[45] Date of Patent: May 14, 1991

[54] ANTIPSYCHOTIC 3-PIPERAZINYLBENZAZOLE DERIVATIVES

[75] Inventors: Ludo E. J. Kennis, Turnhout; Jan Vandenberk, Beerse; Josephus C. Mertens, Oud-Turnhout, all of Belgium

[73] Assignee: Janssen Pharmaceutica N.V., Beerse, Belgium

[21] Appl. No.: 535,931

[22] Filed: Jun. 11, 1990

Related U.S. Application Data

[60] Division of Ser. No. 366,103, Jun. 14, 1989, Pat. No. 4,957,916, which is a continuation-in-part of Ser. No. 228,417, Aug. 5, 1988, abandoned.

[51] Int. Cl.$^5$ .............. A61K 31/495; A61K 31/415; C07D 231/56; C07D 295/18
[52] U.S. Cl. .................... 544/366; 544/282; 544/284; 544/371
[58] Field of Search ............... 544/366, 371

[56] References Cited

U.S. PATENT DOCUMENTS

| | | | |
|---|---|---|---|
| 4,411,901 | 10/1983 | Temple, Jr. et al. | 544/368 |
| 4,452,799 | 6/1984 | Temple, Jr. et al. | 544/368 |
| 4,524,206 | 6/1985 | New et al. | 544/230 |
| 4,581,171 | 4/1986 | Kennis et al. | 514/258 |
| 4,590,196 | 5/1986 | Smith et al. | 514/253 |
| 4,737,500 | 4/1988 | Sosj | 544/284 |
| 4,745,117 | 5/1988 | Ishizumi et al. | 514/254 |
| 4,804,663 | 2/1989 | Kennis | 514/258 |
| 4,957,916 | 9/1990 | Kennis | 544/284 |

FOREIGN PATENT DOCUMENTS

| | | |
|---|---|---|
| 135781 | 4/1985 | European Pat. Off. |
| 281309 | 9/1988 | European Pat. Off. |
| EP-A 0302423 | 2/1989 | European Pat. Off. |
| 197269 | 12/1982 | Japan . |

OTHER PUBLICATIONS

Strupczewski, Chem. Abst., 110-212857z (1989).
Strupczewski, Chem. Abst., 103-123473i (1985).
Lowe et al., Chem. Abst., 110-39024a (1989).
Lowe et al., Chem. Abst., 111-153842m (1989).
Kennis et al., Chem. Abst., 113-78418p (1990).

*Primary Examiner*—Cecilia Shen
*Attorney, Agent, or Firm*—Charles J. Metz

[57] ABSTRACT

3-Piperazinyl-1,2-benzazoles and their pharmaceutically acceptable acid addition salts having useful antipsychotic properties and being useful in the treatment of a variety of disorders in which serotonin and/or dopamine release is of predominant importance.

3 Claims, No Drawings

ANTIPSYCHOTIC 3-PIPERAZINYLBENZAZOLE DERIVATIVES

CROSS-REFERENCE TO RELATED APPLICATION

This is a division of application Ser. No. 366,103, filed Jun. 14, 1989, now U.S. Pat. No. 4,957,916, which is a continuation-in-part of our application Ser. No. 228,417, filed Aug. 5, 1988, now abandoned.

BACKGROUND OF THE INVENTION

In U.S. Pat. Nos. 4,452,799; 4,524,206 and 4,590,196 there are described a number of 3-piperazinyl-1,2-benzisoxazoles and -1,2-benzisothiazoles having psychotropic, tranquilizing and analgesic properties. In U.S. Pat. No. 4,804,663 there are described 3-piperidinyl-1,2-benzisoxazoles and -1,2-benzisothiazoles as antipsychotics. In U.S. Pat. No. 4,745,117 and EP-A-0,281,309 there are described piperazinyl derivatives having antipsychotic properties. In EP-A-0,135,781, published Apr. 3, 1985, there are disclosed a number of 3-piperidinyl-indazole derivatives having antipsychotic and analgesic properties. In EP-A-0,302,423 there are described 1-phenyl-3-piperazinyl-1H-indazole derivatives useful as analgesics, anticonvulsants and antidepressants.

DESCRIPTION OF THE INVENTION

The present invention is concerned with novel 3-piperazinylbenzazoles having the formula

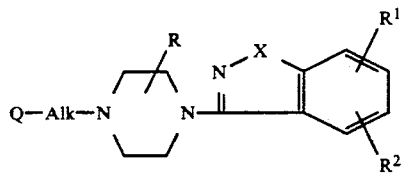

the pharmaceutically acceptable acid addition salts and stereochemically isomeric forms thereof, wherein R is hydrogen or $C_{1-6}$alkyl;
$R^1$ and $R^2$ each independently are hydrogen, halo, hydroxy, $C_{1-6}$alkyloxy or $C_{1-6}$alkyl;
X is O, S or $NR^3$; said $R^3$ being hydrogen, $C_{1-6}$alkyl, aryl or aryl$C_{1-6}$alkyl;
Alk is $C_{1-4}$alkanediyl; and
Q is a radical of formula

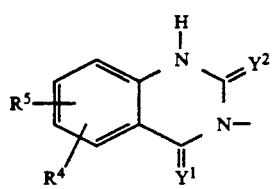

wherein
$Y^1$ and $Y^2$ each independently are O or S;
$R^4$ is hydrogen, halo, $C_{1-6}$alkyl, $C_{1-6}$alkyloxy, trifluoromethyl, nitro, cyano, hydroxy, ($C_{1-10}$alkylcarbonyl)oxy, amino, mono- and di($C_{1-6}$alkyl)amino, ($C_{1-10}$alkylcarbonyl)amino, phenylmethoxy or azido;
$R^5$ is hydrogen or halo; or
Q is a radical of formula

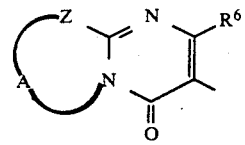

wherein
$R^6$ is hydrogen or $C_{1-6}$alkyl;
Z is —S— or —$CR^7$=$CR^8$—; said $R^7$ and $R^8$ each independently being hydrogen or $C_{1-6}$alkyl; or Z is —$CH_2$— wherein one hydrogen atom may be replaced by hydroxy or $C_{1-6}$alkyl;
A is a bivalent radical —$CH_2$—$CH_2$— or —$CH_2$—$CH_2$—$CH_2$— wherein in the latter two radicals one or two hydrogen atoms may be replaced by $C_{1-6}$alkyl; or A is a bivalent radical —$CR^9$=$CR^{10}$, wherein $R^9$ and $R^{10}$ each independently are hydrogen, halo, amino or $C_{1-6}$alkyl; or when Z is —S— then A may also be —$CR^{11}$=N—, $R^{11}$ being hydrogen or $C_{1-6}$alkyl; or when Z is —$CR^7$=$CR^8$—, then A also may be —O—; and
each aryl is phenyl optionally substituted with up to three substituents independently selected from $C_{1-6}$alkyl, $C_{1-6}$alkyloxy, hydroxy, halo, amino, nitro and trifluoromethyl.

In the foregoing definitions the term halo is generic to fluoro, chloro, bromo and iodo; $C_{1-6}$alkyl defines straight and branched saturated hydrocarbon radicals, having from 1 to 6 carbon atoms, such as, for example, methyl, ethyl, 1-methylethyl, 1,1-dimethylethyl, propyl, butyl, pentyl, hexyl and the like; $C_{1-10}$alkyl defines $C_{1-6}$alkyl radicals as defined hereinabove, and the higher homologs thereof having from 7 to 10 carbon atoms such as, for example, heptyl, octyl, nonyl, decyl and the branched isomers thereof; and $C_{1-4}$alkanediyl radical defines bivalent straight or branch chained alkanediyl radicals having from 1 to 4 carbon atoms, such as, for example, methylene, 1,2-ethanediyl, 1,3-propanediyl, 1,4-butanediyl and the branched isomers thereof.

The moiety Z-A in the radical of formula (b) in particular may be —S—$CH_2$—$CH_2$—, —S—$CH_2$—$CH_2$—$CH_2$—, —S—CH=CH—, —S—CH=C($CH_3$)—, —S—C($CH_3$)=N—, —CH=CH—CH=CH—, —C($CH_3$)=CH—CH=CH—, —CH=CH—C($CH_3$)=CH—, —CH=CH—CCl=CH—, —CH=CH—CBr=CH—, —CH=C($CH_3$)—O—, —$CH_2$—$CH_2$—$CH_2$—$CH_2$—, —CHOH—$CH_2$—$CH_2$—$CH_2$—, —CH($CH_3$)—$CH_2$—$CH_2$—$CH_2$—, —$CH_2$—CH($CH_3$)—$CH_2$—$CH_2$— or —CH($CH_3$)—$CH_2$—CH($CH_3$)—$CH_2$—.

Depending on the nature of the various substituents the compounds of formula (I) may have several asymmetric carbon atoms. Unless otherwise mentioned or indicated, the chemical designation of compounds denotes the mixture of all possible stereochemically isomeric forms, said mixtures containing all diastereomers and enantiomers of the basic molecular structure. The absolute configuration of each chiral center may be indicated by the stereochemical descriptors R and S, this R and S notation corresponding to the rules described in Pure Appl. Chem. 1976, 45, 11–30. Stereochemically isomeric forms of the compounds of formula (I) are obviously intended to be embraced within the scope of the invention.

Pure stereochemically isomeric forms of the compounds of formula (I) may be obtained by the application of art-known procedures. Diastereoisomers may be separated by physical separation methods such as selective crystallization and chromatographic techniques, e.g., counter current distribution, liquid chromatography and the like; and enantiomers may be separated from each other by the selective crystallization of their diastereomeric salts with optically active acids. Pure stereochemically isomeric forms may also be derived from the corresponding pure stereochemically isomeric forms of the appropriate starting materials, provided that the reaction occurs stereospecifically.

Preferred compounds are those compounds of formula (I) wherein R is hydrogen; and/or $R^1$ and $R^2$ each independently are hydrogen, halo or $C_{1-6}$alkyl; and/or Q is a radical of formula (a) wherein $Y^1$ and $Y^2$ are oxygen, and $R^4$ and $R^5$ are hydrogen, or Q is a radical of formula (b) wherein $R^6$ is $C_{1-6}$alkyl.

Particularly preferred compounds are those preferred compounds wherein $R^2$ is hydrogen or halo; and/or X is O, S or NH; and/or Q is a radical of formula (b), Z is —S— or —$CR^7$=CH—, said $R^7$ being hydrogen or $C_{1-6}$alkyl, or Z is $CH_2$ wherein one hydrogen atom may be replaced by $C_{1-6}$alkyl; and A is —$CH_2$—$CH_2$— or —$CH_2$—$CH_2$—$CH_2$—, wherein in each of the latter two radicals one or two hydrogen atoms may be replaced by $C_{1-6}$alkyl, or A is —$CR^9$=$CR^{10}$—, said $R^9$ and $R^{10}$ each independently being hydrogen or $C_{1-6}$alkyl.

More particularly preferred compounds are those particularly preferred compounds wherein $R^1$ is hydrogen, fluoro or methyl; and/or $R^2$ is hydrogen; and/or —Z—A— is —S—$CH_2$—$CH_2$—, —S—$CH_2$—$CH_2$—$CH_2$—, —S—CH=$CR^{10}$—, —$CH_2$—$CH_2$—$CH_2$—$CH_2$—, —CH($CH_3$)—$CH_2$—$CH_2$—$CH_2$—, —C($CH_3$)=CH—CH=CH— or —CH=CH—CH=$CR^{10}$—, $R^{10}$ being hydrogen or methyl.

The most preferred compounds are those more particularly preferred compounds wherein X is O or NH; and/or $R^1$ is hydrogen or 6-fluoro.

The compounds of formula (I) can generally be prepared by reacting a piperazinebenzazole of formula (III) with an alkylating reagent of formula (II). In formula (II) W represents a reactive leaving group such as, for example, halo, e.g., chloro, bromo or iodo, or a sulfonyloxy group, e.g. methanesulfonyloxy, 4-methylbenzenesulfonyloxy and the like leaving groups.

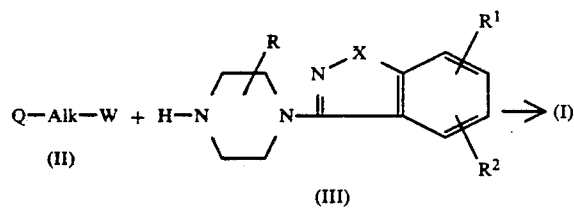

Said N-alkylation reaction can conveniently be conducted in a reaction-inert organic solvent such as, for example, an aromatic hydrocarbon, e.g., benzene, methylbenzene, dimethylbenzene and the like; a lower alkanol, e.g. methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; a dipolar aprotic solvent, e.g. N,N-dimethylformamide, N,N-dimethylacetamide, nitrobenzene, 1-methyl-2-pyrrolidinone and the like; or a mixture of such solvents. The addition of an appropriate base such as, for example, an alkali or an earth alkaline metal carbonate, hydrogen carbonate, hydroxide, alkoxide or hydride, e.g., sodium carbonate, sodium hydrogen carbonate, potassium carbonate, sodium hydroxide, sodium methoxide, sodium hydride and the like, or an organic base such as, for example an amine, e.g., N,N-diethylethanamine, N-(1-methylethyl)-2-propanamine, 4-ethylmorpholine and the like, may be utilized to pick up the acid which is liberated during the course of the reaction. In some circumstances the addition of a iodide salt, preferably an alkali metal iodide, is appropriate. Somewhat elevated temperatures may enhance the rate of the reaction. In this and the following preparations, the reaction products may be isolated from the reaction mixture and, if necessary, further purified according to methodologies generally known in the art, such as, for example, extraction, destillation, crystallization, trituration and chromatography.

The compounds of formula (I) may also be prepared by N-alkylating a piperazine derivative of formula (IV) with a benzazole of formula (V),

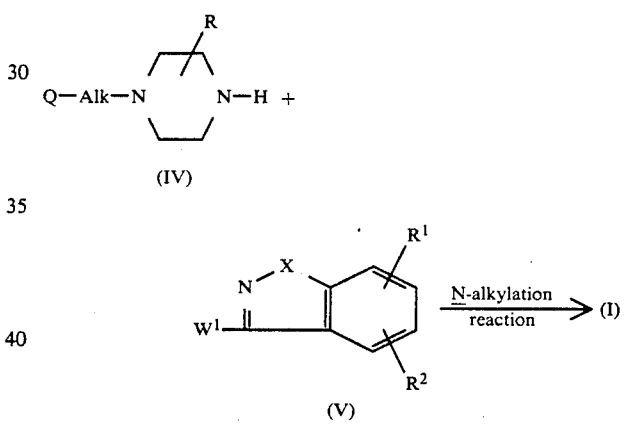

wherein $W^1$ represents a suitable leaving group such as halo, e.g. chloro or bromo. Said N-alkylation reaction of (IV) with (V) may be carried out following the same procedure as described hereinabove for the preparation of compounds of formula (I) from the intermediates (II) and (III).

The compounds of formula (I) wherein X is oxygen or $NR^3$, said X being represented by $X^1$ and said compounds by formula (I-a), can also be obtained by the cyclization of an intermediate of formula (VI) upon treatment with an appropriate base in a reaction-inert solvent.

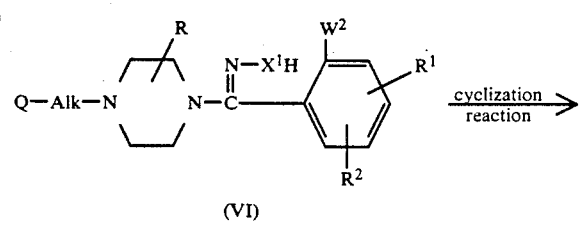

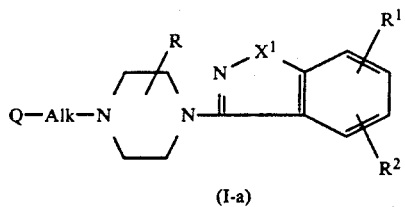

(I-a)

In formula (VI) $W^2$ represents a suitable leaving group such as halo, e.g. fluoro or chloro, or a nitro group. Appropriate bases for said cyclization are, for example, alkali and earth alkaline metal carbonates, hydrogen carbonates, hydroxides, alkoxides or hydrides, e.g. sodium carbonate, sodium hydrogen carbonate, potassium carbonate, sodium hydroxide, sodium methoxide, sodium hydride or organic bases such as amines, e.g. N,N-diethylethanamine, 4-ethylmorpholine and the like bases. Suitable solvents are, for example, aromatic hydrocarbons, e.g. benzene, methylbenzene, dimethylbenzene and the like; lower alkanols, e.g. methanol, ethanol, 1-butanol and the like; ketones, e.g. 2-propane, 4-methyl-2-pentanone and the like; ethers, e.g. 1,4-dioxane, tetrahydrofuran and the like; dipolar aprotic solvents, e.g. N,N-dimethylformamide, N,N-dimethylacetamide, dimethylsulfoxide, 1-methyl-2-pyrrolidinone and the like or mixtures of such solvents. In order to enhance the rate of the reaction, the temperature of the reaction mixture may be raised and particularly, said cyclization may be conducted at the reflux temperature of the reaction mixture.

The compounds of formula (I-a) wherein $X^1$ is O, said compounds being represented by formula (I-a-1) can also be obtained by cyclizing an activated oxime derivative of formula (VII).

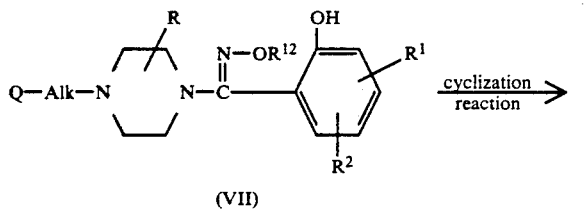

(VII)

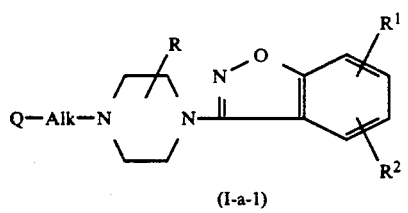

(I-a-1)

wherein $R^{12}$ is formyl, ($C_{1-6}$alkyl or aryl)carbonyl, e.g. acetyl, propionyl, benzoyl and the like; ($C_{1-6}$alkyl or aryl)oxycarbonyl, e.g. methoxycarbonyl, ethoxycarbonyl, (1,1-dimethyl)ethoxycarbonyl, phenyloxycarbonyl and the like; ($C_{1-6}$alkyl or aryl)sulfonyl, e.g. methanesulfonyl, benzenesulfonyl, 4-methylbenzenesulfonyl, 2-naphthalenesulfonyl and the like; N-acylaminocarbonyl, e.g. trichloromethylcarbonylaminocarbonyl and the like. Said cyclization reaction of the activated oxime derivative of formula (VII) may conveniently be conducted by treatment with an appropriate base, preferably in a suitable reaction-inert solvent, at temperatures in the range from 20° to 200° C., particularly from 50° to 150° C. and preferably at the reflux temperature of the reaction mixture. In some instances however, it may be advantageous not to add a base to the reaction mixture and to remove the acid liberated during the reaction by destillation at normal pressure or, if desired, at reduced pessure. Alternatively, said cyclization may also be effected by heating the oxime derivative (VII) in vacuo without a solvent. Appropriate bases are for example, alkali and earth alkaline metal carbonates, hydrogen carbonates and amines, e.g. sodium carbonate, potassium carbonate, sodium hydrogen carbonate, N,N-diethylethanamine, 4-ethylmorpholine, 1,4-diazabicylco[2.2.2]octane, pyridine and the like bases. Suitable solvents for said cyclization are, for example, aromatic hydrocarbons, e.g. benzene, methylbenzene, dimethylbenzene and the like; ethers, e.g. 1,1'-oxybisethane, 1,1'-oxybisbutane, tetrahydrofuran, 1,4-dioxane, 2,2'-oxybis[methoxyethane], 2,5,8,11-tetraoxadodecane and the like; dipolar aprotic solvents, e.g. N,N-dimethylformamide, N,N-dimethylacetamide, 1-methyl-2-pyrrolidinone, hexamethylphosphoric triamide, pyridine, acetic anhydride and the like; halogenated hydrocarbons, e.g. trichloromethane, tetrachloromethane, 1,2-dichloroethane, chlorobenzene and the like solvents.

The compounds of formula (I) wherein $R^3$ is other than hydrogen, said radical being represented by $R^{3-a}$ and said compounds by formula (I-b-1), can be obtained by N-alkylating a compound of formula (I-b-2), which is a compound of formula (I) wherein $R^3$ is hydrogen, with an alkylating reagent of formula $R^{3-a}W$ (VIII), wherein W is a reactive leaving group as defined hereinabove.

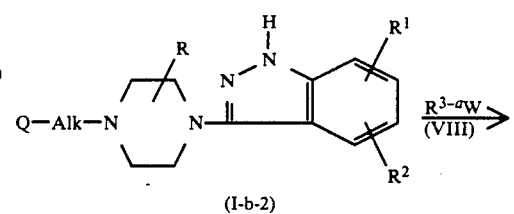

(I-b-2)

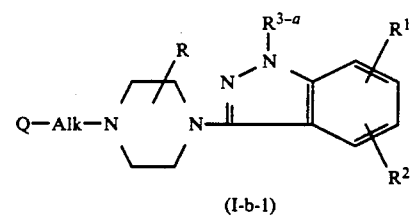

(I-b-1)

Said N-alkyation reaction may be conducted following the same procedures described hereinabove for the preparation of the compounds of formula (I) from the intermediates (II) and (III).

The compounds of formula (I) may also be prepared following art-known procedures for building up radicals of formula Q.

For example, the compounds of formula (I) wherein Q is a radical of formula (a), said compounds being represented by the formula (I-c), can be prepared by cyclizing an appropriate 2-aminobenzamide or 2-aminobenzenethioamide of formula (IX) with a reagent of formula (X).

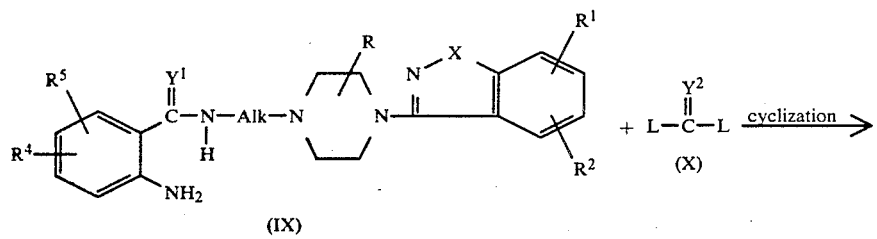

(IX)

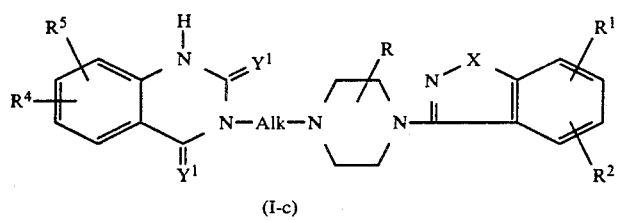

(I-c)

In said reagent of formula (X), $Y^2$ is oxygen or sulfur and each L independently is a reactive leaving group such as, for example, halo, e.g. chloro or bromo, $C_{1-6}$alkyloxy, e.g. methoxy, ethoxy, and the like; aryloxy, e.g. phenoxy and the like; amino; mono-and di($C_{1-6}$alkyl)amino, e.g. methylamino, diemthylamino and the like; 1H-imidazol-1-yl, and the like leaving groups.

The compounds of formula (I-c) can also be prepared by cyclizing an appropriately substituted intermediate of formula (XI) with an amine of formula (XII).

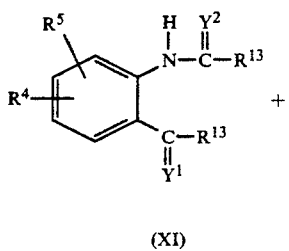

(XI)

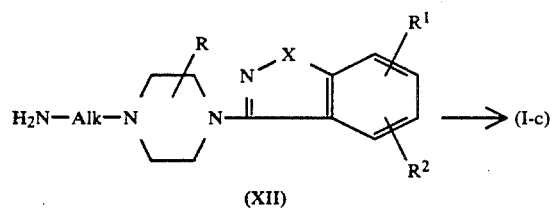

(XII)

or by cyclizing an isocyanate or isothiocyanate of formula (XIII) with an amine of formula (XII).

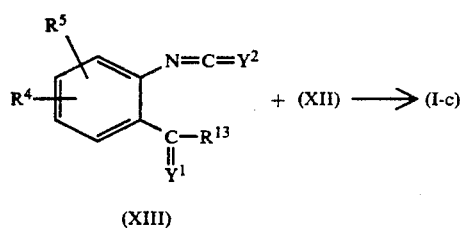

(XIII)

Said cyclization reactions can conveniently be conducted by stirring and, if desired, heating the reactants, optionally in a suitable reaction-inert solvent having a relatively high boiling point such as an aliphatic or aromatic hydrocarbon, e.g. petroleum ether, dimethylbenzene and the like.

In the foregoing reaction schemes each $R^{13}$ independently represents an appropriate leaving group such as, for example, $C_{1-6}$alkyloxy, amino, or mono- and di($C_{1-6}$alkyl)amino; in formula (XI) both $R^{13}$ groups taken together may also represent —O—.

The compounds of formula (I) wherein Q is a radical of formula (b), said compounds being represented by the formula (I-d), can be prepared following art-known cyclizing procedures for preparing pyrimidin-4-ones such as, for example, by reacting an amine of formula (XIV) with a β-dicarbonyl intermediate of formula (XV) or by cyclizing a reagent of formula (XVI) with an amine of formula (XVII).

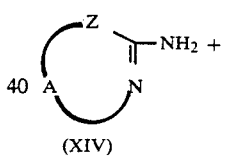

(XIV)

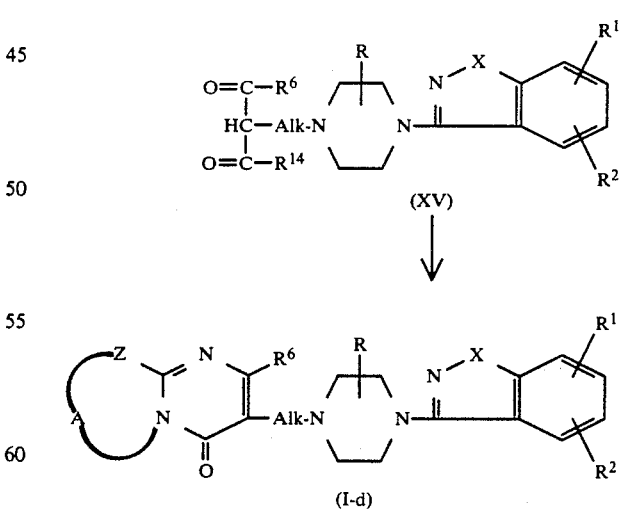

(XV)

(I-d)

(XVI)

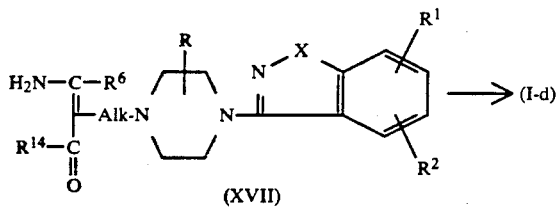

(XVII) → (I-d)

Said cyclization reactions may generally be carried out by stirring the reactants, if desired, in the presence of a suitable reaction-inert solvent such as, for example, an aliphatic, alicyclic or aromatic hydrocarbon, e.g., hexane, cyclohexane, benzene and the like; pyridine; N,N-dimethylformamide and the like dipolar aprotic solvents. Elevated temperatures may be appropriate to enhance the reaction-rate. In some cases it may be preferable to carry out the reaction at the reflux temperature of the reaction mixture.

In the foregoing reaction schemes each $R^{14}$ independently represents an appropriate leaving group such as, for example, ($C_{1-6}$alkyl)oxy, hydroxy, halo, amino, mono- and di($C_{1-6}$alkyl)amino and the like.

Following the same cyclization procedures, the compounds of formula (I-d) can also be prepared by cyclizing an intermediate of formula (XVII) with a reagent of formula (XVIII).

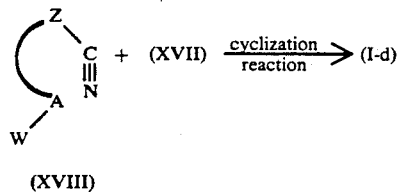

(XVIII)

The compounds of formula (I-d) wherein Z is S and A is —$CH_2$—$CH_2$— or —$CH_2$—$CH_2$—$CH_2$—, each of the latter radicals being optionally substituted with one or two $C_{1-6}$alkyl groups, said compounds being represented by the formula (I-d-1), can also be prepared by cyclizing a 2-mercaptopyrimidinone of formula (XIX) with a reagent of formula (XX), wherein each W independently has the same meaning as previously described.

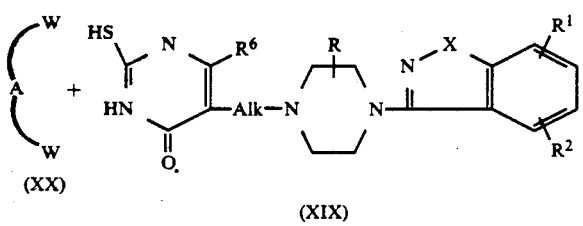

(XX)     (XIX)

↓ cyclization reaction

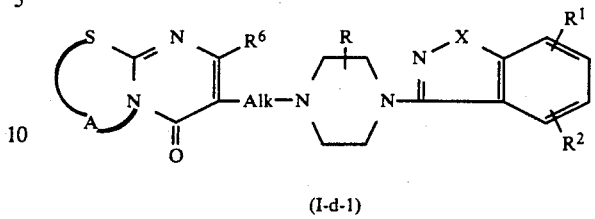

(I-d-1)

The compounds of formula (I-d) wherein Z is S and A is —$CR^9$=$CR^{10}$—, said compounds being represented by the formula (I-d-2), can be prepared by cyclizing a 2-mercaptopyrimidinone of formula (XIX) with a reagent of formula (XXI).

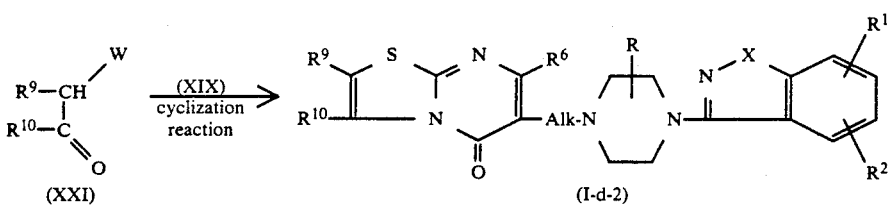

(XXI)     (I-d-2)

The cyclization reactions for preparing the compounds of formulae (I-d-1) and (I-d-2) may generally be carried out by stirring the reactants, if desired, in the presence of a suitable reaction-inert solvent such as, for example, an aliphatic, alicyclic or aromatic hydrocarbon, e.g., hexane, cyclohexane, benzene and the like; pyridine; N,N-dimethylformamide and the like dipolar aprotic solvents. Elevated temperatures may be appropriate to enhance the reaction rate. In some cases it may be preferably to carry out the reaction at the reflux temperature of the reaction mixture.

The compounds of formula (I) may also be converted into each other following art-known functional group transformation procedures.

For example, the compounds of formula (I-c) wherein $R^4$ is amino, may be derived from the corresponding nitro-substituted quinazolines following art-known nitro-to-amine reduction procedures. A suitable nitro-to-amine reduction procedure is, for example, catalytic hydrogenation in a relatively polar solvent such as, for example, an alcohol, e.g. methanol or ethanol, in the presence of an appropriate catalyst, e.g. platinum-on-charcoal. In some cases it may be useful to add an appropriate catalyst poison such as thiophene.

The compounds of formula (I-c) wherein $R^4$ is phenylmethoxy may be converted into compounds of formula (I-c) wherein $R^4$ is hydroxy following art-known catalytic hydrogenolysis procedures; the compounds of formula (I-c) wherein $R^4$ is amino or hydroxy may be converted into compounds of formula (I-c) wherein $R^4$ is ($C_{1-10}$alkylcarbonyl)amino or ($C_{1-10}$alkylcarbonyl)oxy respectively, by reacting the former compouns with a suitable acylating agent such as an acylhalide or an acid anhydride; the compounds of formula (I-c) wherein $R^4$ is amino may be converted into compounds of formula (I-c) wherein $R^4$ is azido by converting the amino group into a diazonium group with nitrous acid or an appropriate alkali metal or earth alkaline metal thereof and subsequently converting said diazonium group into an azide group with sodium azide or any other suitable alkali metal or earth alkaline metal azide.

The compounds of formula (I) have basic properties and, consequently, they may be converted to their therapeutically active non-toxic acid addition salt forms by treatment with appropriate acids, such as, for example, inorganic acids, e.g. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted into the free base form by treatment with alkali.

The term acid addition salt as used hereinabove also comprises the solvates which the compounds of formula (I) are able to form and said solvates are meant to be included within the scope of the present invention. Examples of such solvates are e.g., the hydrates, alcoholates and the like.

A number of intermediates and starting materials in the foregoing preparations are known compounds which may be prepared according to art-known methodologies of preparing said or similar compounds. For example, some of the intermediates of formula (III) and (V) and their preparations are described in U.S. Pat. Nos. 4,452,799, 4,524,206 and 4,590,196 and in EP-A-0,302,423; the intermediates of formula (II) and their preparations are described in U.S. Pat. No. 4,804,663, and in the references cited therein. Other intermediates may be prepared according to art-known methodologies of preparing similar compounds and for some of them, preparative methods are presented hereinafter.

The intermediates of formula (III) wherein X is NR³ and R³ is other than aryl, said radical being represented by R³⁻ᵇ and, said compounds being represented by formula

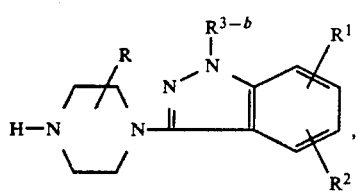

are novel and can be obtained by deprotecting an intermediate of formula

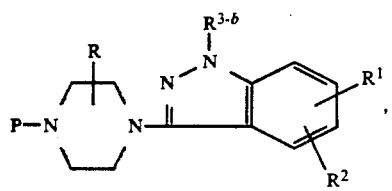

wherein P represents a protective group such as, for example, (C₁₋₆alkyl or aryl)carbonyl, (C₁₋₆alkyloxy or aryloxy)carbonyl or phenylmethyl, by acid or base hydrolysis or catalytic hydrogenation. The protected intermediate of formula (XXII) can be prepared from a thioamide of formula

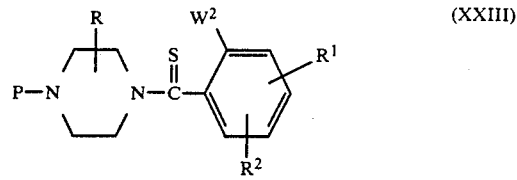

wherein W² represents a reactive leaving group as defined hereinabove, by the condensation with a hydrazine derivative of formula R³⁻ᵇ—NH—NH₂ (XXIV) in the presence of an acid such as acetic acid and subsequent cyclization in alkali. Said thioamide of formula (XXIII) in turn, is accessible from an amide of formula

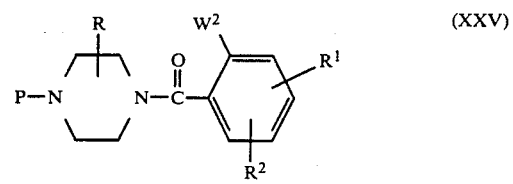

by the reaction with 2,4-bis(4-methoxyphenyl)-2,4-disulfide-1,3,2,4-dithiaphosphetane (Lawesson's Reagent).

The amide of formula (XXV) may be prepared by N-acylating a mono-protected piperazine (XXVI) with a carboxylic acid of formula (XXVII) or a functional derivative thereof such as, for example, a halide, a symmetrical or mixed anhydride following art-known N-acylation procedures.

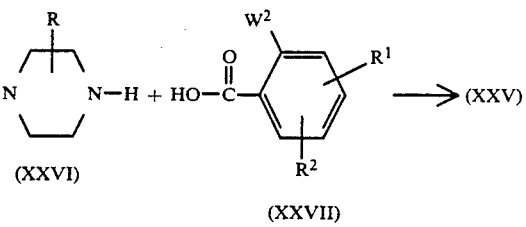

The intermediates of formula (VI) wherein X¹ is oxygen, said intermediates being represented by formula (VI-a) may generally be derived from the above-defined alkylating reagent of formula (II) and an amidoxime of formula (XXVIII) following the N-alkylation procedures described for the preparation of the compounds of formula (I) from the intermediates (II) and (III).

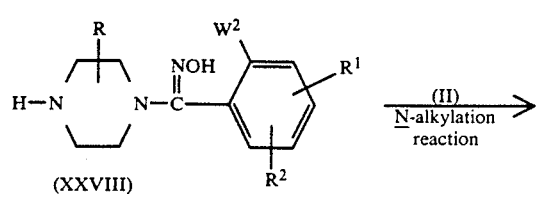

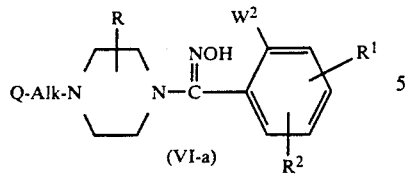

(VI-a)

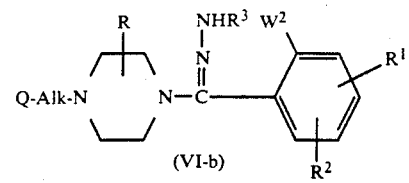

(VI-b)

The reagent (XXVIII) in turn, is easily accessible from an appropriately substituted benzaldehyde oxime of formula

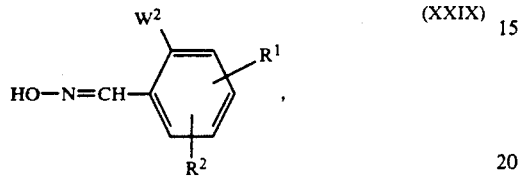

by treating a solution of said oxime (XXIX) in a reaction-inert solvent with chlorine gas, followed by an elimination of hydrogen chloride from the thus obtained intermediate of formula

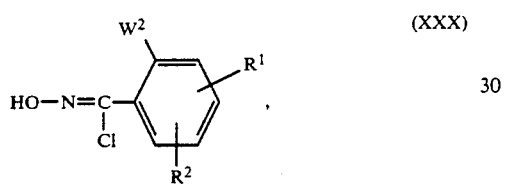

upon treatment with an appropriate base such as a trialkylamine, e.g. N,N-diethylethanamine, and treating the resulting nitrile N-oxide of formula

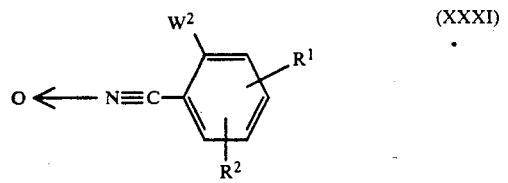

with piperazine. An important feature of this reaction sequence is the fact that the intermediates (XXX) and (XXXI) need not be purified nor isolated before further conversion to the intermediate (XXVIII).

The intermediates of formula (VI) wherein $X^1$ is $NR^3$, said intermediates being represented by formula (VI-b) can be obtained by N-alkylating an appropriately substituted hydrazonamide of formula (XXXII) with an alkylating reagent of formula (II) following the procedures described hereinabove for the preparation of the compounds of formula (I) from the intermediates (II) and (III).

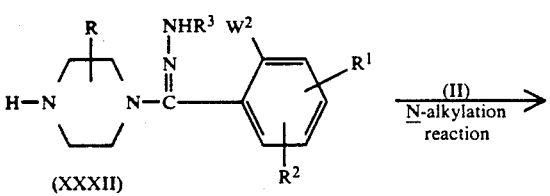

The intermediate (XXXII) can be prepared by treating piperazine with a reagent of formula

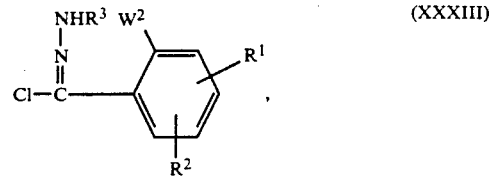

which in turn is obtained upon halogenating a hydrazide of formula

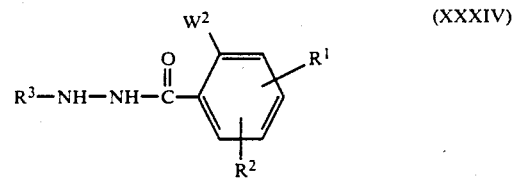

with a halogenating reagent such as pentachlorophosphorane, phosphorous trichloride and the like reagents.

The compounds of formula (I), the pharmaceutically acceptable acid addition salts and stereochemically isomeric forms thereof, are potent antagonists of neurotransmitters and in particular of the mediators serotonin and dopamine. Antagonizing said mediators will suppress or relieve a variety of symptoms associated with phenomena induced by the release, in particular the excessive release, of these mediators. Therapeutic indications for using the present compounds are mainly in the CNS area, the gastrointestinal and cardiovascular field and related domains. Serotonin antagonists are reportedly effective in combatting psychoses, aggressive behaviour, anxiety, depression and migraine. Dopamine receptor antagonists are known to have neuroleptic properties. Combined serotin-dopamine antagonists are especially interesting as they appear to offer relief of both the positive and negative symptoms of schizophrenia. Further the present compounds also appear to be useful therapeutic agents for combatting autism. Therapeutic applications in the gastrointestinal field comprise their use as, for instance, antidiarrhoeals, inhibitors of gastro-oesophageal reflux and particularly antiemetics, e.g. in cancer patients receiving chemotherapy and radiation treatment. Further, serotonin is a potent broncho- and vasoconstrictor and thus the present antagonists may be used against hypertension and vascular disorders. In addition, serotonin antagonists have been associated with a number of other properties such as, the suppression of appetite and promotion of weight loss, which may prove effective in combatting obesity; and also the alleviation of withdrawal symptoms in addicts trying to discontinue drinking and smoking habits.

In view of their useful pharmacological properties, the subject compounds may be formulated into various pharmaceutical forms for administration purposes. To prepare the pharmaceutical compositions of this invention, an effective amount of the particular compound, in base or acid addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In view of the usefulness of the subject compounds in the treatment of psychotic diseases it is evident that the present invention provides a method of treating warmblooded animals suffering from psychotic diseases, said method comprising the systemic administration of an antipsychotic effective amount of a compound of formula (I) or a pharmaceutically acceptable acid addition salt thereof in admixture with a pharmaceutical carrier. Those of skill in the treatment of psychotic diseases could easily determine the effective amount from the test results presented here. In general it is contemplated that an effective amount would be from 0.01 mg/kg to 4 mg/kg body weight, more preferably from 0.04 mg/kg to 2 mg/kg body weight.

The following examples are intended to illustrate and not to limit the scope of the present invention. Unless otherwise stated all parts therein are by weight.

EXPERIMENTAL PART

A. Preparation of Intermediates

EXAMPLE 1

(a) To a stirred mixture of 114 parts of 1,2-benzisoxazol-3-ol and 230 parts of phosphoryl chloride were added dropwise 160 parts of N,N-diethylethanamine (exothermic reaction). Upon complete addition, the reaction mixture was stirred overnight at 135° C. The mixture was poured into crushed ice and the product was extracted with trichloromethane. The extract was dried, filtered and evaporated. The residue was boiled in 2,2'-oxybispropane. The solvent was decanted (this was repeated twice) and the residue was purified by column chromatography over silica gel using a mixture of trichloromethane and methanol (97:3 by volume) as eluent. The pure fractions were collected and the eluent was evaporated, yielding 60 parts (51.1%) of 3-chloro-7-methyl-1,2-benzisoxazole as a residue (int. 1).

(b) To a stirred and heated (90° C.) mixture of 120 parts of piperazine and 400 parts of 1-butanol were added dropwise 60 parts of 3-chloro-7-methyl-1,2-benzisoxazole. Upon complete addition, stirring was continued for 6 hours at reflux temperature. After cooling, the reaction mixture was filtered and the filtrate was evaporated. The residue was taken up in water and the product was extracted with trichloromethane. The extract was dried, filtered and evaporated. The residue was purified by column chromatography over silica gel using a mixture of trichloromethane and methanol (95:5 by volume) as eluent. The pure fractions were collected and the eluent was evaporated. The residue was solidified on standing, yielding 56 parts (71.5%) of 7-methyl-3-(1-piperazinyl)-1,2-benzisoxazole as a residue (int. 2).

EXAMPLE 2

(a) A mixture of 32 parts of ethyl 1-piperazinecarboxylate, 17 parts of 3-chloro-1,2-benzisothiazole and 45 parts of N,N-dimethylacetamide was stirred for 0.5 hours at 150° C. After cooling to 50° C., the reaction mixture was poured into ice water. The aqueous layer was decanted and the oily layer was stirred in water. The product from the oil layer was extracted with trichloromethane. The extract was dried, filtered and evaporated. The residue was purified by column chromatography over silica gel using a mixture of trichloromethane and methanol (95:5 by volume) as eluent. The pure fractions were collected and the eluent was evaporated, yielding 13 parts (44%) of ethyl 4-(1,2-benzisothiazol-3-yl)-1-piperazinecarboxylate as a residue (int. 3).

(b) A mixture of 12.5 parts of ethyl 4-(1,2-benzisothiazol-3-yl)-1-piperazinecarboxylate and 187.5 parts of a hydrobromic acid solution 48% in water was stirred for 1.5 hours at reflux temperature. After evaporation, the residue was taken up in 2-propanol and the solvent was evaporated again. The residue was dissolved in methanol, evaporated again and stirred in 2-propanone. The product was filtered off and dried, yielding 11.5 parts (73%) of 3-(1-piperazinyl)-1,2-benzisothiazole dihydrobromide (int. 4).

EXAMPLE 3

(a) To a stirred and cooled mixture (10° C.) of 64 parts of 1-(phenyl-methyl)piperazine and 360 parts of tetrahydrofuran were added during 20 minutes 32.5 parts of 2,4-difluorobenzoyl chloride. Upon complete addition, stirring was continued until room temperature. The formed salt was filtered off and the filtrate was evaporated in vacuo. The residue was purified by column chromatography over silica gel using a mixture of trichloromethane and methanol (95:5 by volume) as eluent. The pure fractions were collected and the eluent was evaporated, yielding 50 parts (87.8%) of 1-(2,4-difluorobenzoyl)-4-(phenylmethyl)-piperazine as a residue (int. 5).

(b) A mixture of 30 parts of 1-(2,4-difluorobenzoyl)-4-(phenylmethyl)-piperazine, 19 parts of 2,4-bis(4-methoxyphenyl)-2,4-disulfide-1,3,2,4-dithiaphosphetane and 174 parts of benzene was stirred and refluxed for 3 hours. The reaction mixture was evaporated and the residue was dissolved in trichloromethane. The residue was purified by column chromatography over silica gel using trichloromethane as eluent. The pure fractions were collected and the eluent was evaporated in vacuo. The residue was allowed to stand for 2 days at room temperature. The product was filtered off and dried, yielding 25 parts (79.2%) of 1-[(2,4-difluorophenyl)thioxomethyl]-4-(phenyl-methyl)piperazine (int. 6).

(c) A mixture of 40 parts of 1-[(2,4-difluorophenyl)-thioxomethyl]-4-(phenylmethyl)piperazine, 144 parts of 1-butanol, 13 parts of hydrazine monohydrate and 24 parts of acetic acid was stirred overnight at reflux temperature. After cooling, 50 parts of sodium carbonate were added and stirring was continued for 3 hours at reflux temperature. The reaction mixture was cooled until room temperature and water and methylbenzene were added. After stirring for 15 minutes, the separated organic layer was dried, filtered and evaporated. The residue was purified by column chromatography over silica gel using a mixture of trichloromethane and methanol (92:8 by volume) as eluent. The pure fractions were collected and the eluent was evaporated. The residue was crystallized from acetonitrile. The product was filtered off and dried, yielding 12 parts (32.2%) of 6-fluoro-3-[4-(phenylmethyl)piperazinyl]-1H-indazole; mp. 162.0° C. (int. 7).

(d) A mixture of 12 parts of 6-fluoro-3-[4-(phenylmethyl)-piperazinyl]-1H-indazole, 1 part of Raney nickel catalyst and 200 parts of methanol was hydrogenated in a Parr-apparatus at normal pressure and at 50° C. with 2 parts of palladium-on-charcoal catalyst 10%. After the calculated amount of hydrogen was taken up, the catalyst was filtered off over diatomaceous earth and the filtrate was evaporated in vacuo. The residue was crystallized from acetonitrile. The product was filtered off and dried, yielding 7.7 parts (92.0%) of 6-fluoro-3-(1-piperazinyl)-1H-indazole (int. 8).

EXAMPLE 4

(a) To a stirred mixture of 12.5 parts of piperazine, 3.6 parts of N,N-diethylethanamine and 75 parts of trichloromethane was added a solution of 9 parts of 2-fluoro-N-phenylbenzenecarbohydrazonoyl chloride in 75 parts of trichloromethane. The whole was stirred for 2 hours at room temperature. After the addition of 5 parts of potassium carbonate, the reaction mixture was stirred for 30 minutes at reflux temperature. The mixture was cooled, washed with 100 parts of water and the layers were separated. The organic layer was dried, filtered and evaporated, yielding 6 parts (55.8%) of 1-(2-fluorobenzoyl)-piperazine, 2-phenylhydrazine as a residue (int. 9).

(b) A mixture of 4.5 parts of 3-(2-chloroethyl)-2-methyl-4H-pyrido-[1,2-a]pyrimidin-4-one, 6 parts of 1-(2-fluorobenzoyl)piperazine, 2-phenylhydrazine, 5.04 parts of sodium carbonate, 0.1 parts of potassium iodide and 120 parts of 4-methyl-2-pentanone was stirred overnight at reflux temperature. The inorganic salts were filtered off and the filtrate was evaporated. The residue was purified by column chromatography over silica gel using a mixture of trichloromethane and methanol (95:5 by volume) as eluent. The pure fractions were collected and the eluent was evaporated. The residue was crystallized from 2-propanol. The product was filtered off and dried, yielding 2.5 parts (25.8) of 3-[2-[4-[(2-fluorophenyl)(2-phenylhydrazono)methyl]-1-piperazinyl]ethyl]-2-methyl-4H-pyrido[1,2-a]pyrimidin-4-one; mp. 180° C. (int. 10).

EXAMPLE 5

(a) A mixture of 98 parts of 2,4-difluorobenzaldehyde, 49 parts of hydroxylamine monohydrochloride, 160 parts of methanol and 80 parts of 2-propanol, saturated with hydrochloric acid was stirred and refluxed for 4 hours. The reaction mixture was concentrated in vacuo and the residue was triturated in 2,2'-oxybispropane. The product was filtered off and dried, yielding 60 parts (45.0%) of 2,4-difluorobenzaldehyde, oxime hydrochloride (int. 11).

(b) Through a stirred and cooled (−10° C.) mixture of 58 parts of 2,4-difluorobenzaldehyde, oxime hydrochloride and 750 parts of trichloromethane was bubbled chlorine during 30 minutes. The excess of chlorine was removed with a stream of nitrogen and 42 parts of N,N-diethylethanamine were added dropwise to the solution. Upon completion, stirring was continued, while allowing the reaction mixture to reach room temperature. The precipitate was filtered off. The filtrate was cooled to −20° C. and was added to a stirred and cooled (−10° C.) solution of 86 parts of piperazine in 900 parts of trichloromethane during 10 minutes. The reaction mixture was stirred overnight at room temperature. Then the mixture was heated till 30° C. and filtered. The filtrate was concentrated in vacuo at 25° C. The excess of piperazine was removed by washing twice with 100 parts of water. The separated organic layer was dried, filtered and concentrated in vacuo. The concentrate was triturated in 2,2'-oxybispropane. The solid product was filtered off and dried, yielding 50 parts (69.1%) of 1-[(2,4-difluorophenyl)(hydroxylimino)methyl]piperazine (int. 12).

(c) A mixture of 8 parts of 6-(2-bromoethyl)-2,3-dihydro-7-methyl-5H-thiazolo[3,2-a]pyrimidin-5-one monohydrobromide, 4.8 parts of 1-[(2,4-difluorophenyl)(hydroxyimino)methyl]piperazine, 8 parts of sodium hydrogen carbonate and 180 parts of 4-methyl-2-pentanone was stirred for 20 hours at reflux temperature. The reaction mixture was filtered while hot and the filtrate was evaporated in vacuo. The residue was purified by column chromatography over silica gel using a mixture of trichloromethane and methanol (95:5 by volume) as eluent. The pure fractions were collected and the eluent was concentrated in vacuo. The residue was crystallized from acetonitrile. The product was filtered off and dried, yielding 4.4 parts (50.5%) of 6-[2-[4-[(2,4-difluorophenyl)-(hydroxyimino)methyl]-1-piperazinyl]ethyl]-2,3-dihydro-7-methyl-5H-thiazolo[3,2-a]pyrimidin-5-one (int. 13).

EXAMPLE 6

A mixture of 58 parts of 5-methyl-1,3,4-thiadiazol-2-amine, 76 parts of 3-acetyl-4,5-dihydro-2(3H)-furanone, 1.2 parts of hydrochloric acid solution 12N and 540 parts of methylbenzene was stirred and refluxed for 2 hours using a water-separator. After cooling to room temperature, there were added dropwise 340 parts of phosphoryl chloride at 20°–40° C. (cooling was necessary to keep that temperature). The whole was gradually heated to reflux: at 95° C. Hydrogen chloride gas evolution was started. Then 100 parts of the mixture were distilled off and the residue was stirred and refluxed for 2 hours. After cooling, the reaction mixture was evaporated and the residue was poured into an ice/ammonium hydroxide mixture while stirring. The product was extracted with trichloromethane. The extract was dried, filtered and evaporated. The residue was purified three times by column-chromatography over silica gel using each time a mixture of trichloromethane and methanol (95:5 by volume) as eluent. The pure fractions were collected and the eluent was evaporated. The residue was crystallized from 2,2′-oxybispropane, yielding 11.8 parts of 6-(2-chloroethyl)-2,7-dimethyl-5H-1,3,4-thiadiazolo[3,2-a]pyrimidin-5-one; mp. 118° C. (int. 14).

EXAMPLE 7

(a) A mixture of 50 parts of 5-methyl-3-isoxazolamine, 70 parts of 3-acetyl-4,5-dihydro-2(3H)-furanone, 435 parts of methylbenzene and 16 parts of polyphosphoric acid was stirred and refluxed for 3 hours using a water separator. The reaction mixture was concentrated in vacuo, yielding 99 parts (95.1%) of 4,5-dihydro-3-[1-(5-methyl-3-isoxazolyl)imino]ethyl]-2(3H)-furanone as an oily residue (int. 15).

(b) To a stirred mixture of 98 parts of 4,5-dihydro-3-[1-(5-methyl-3-isoxazolyl)imino]-ethyl]-2(3H)-furanone, 348 parts of methylbenzene and 300 parts of trichloromethane were added dropwise 150 parts of phosphoryl chloride. Upon complete addition, stirring was continued for 3 hours at reflux temperature. The reaction mixture was concentrated until half its volume and the residue was poured into crused ice. The whole was treated with an ammonium hydroxide solution and the product was extracted twice with 240 parts of 4-methyl-2-pentanone. The combined extracts were dried, filtered and evaporated in vacuo. The residue was dissolved in trichloromethane, filtered over silica gel and the filtrate was concentrated in vacuo. The residue was crystallized form a mixture of methylbenzene and 2,2′-oxybispropane, yielding 96 parts (88.2%) of 6-(2-chloroethyl)-2,5-dimethyl-7H-isoxazolo[2,3-a]pyrimidin-7-one; mp. 165° C. (int. 16).

B. Preparation of Final Compounds

EXAMPLE 8

A mixture of 5 parts of 3-(2-chloroethyl)-6,7,8,9-tetrahydro-2-methyl-4H-pyrido[1,2-a]-pyrimidin-4-one monohydrochloride, 5 parts of 3-(1-piperazinyl)-1,2-benzisothiazole dihydrochloride, 8 parts of sodium carbonate, 0.2 parts of potassium iodide and 200 parts of 4-methyl-2-pentanone was stirred for 20 hours at reflux temperature. The reaction mixture was filtered and the filtrate was evaporated. The residue was purified by column chromatography over silica gel using a mixture of trichloromethane and methanol (95:5 by volume) as eluent. The pure fractions were collected and the eluent was evaporated. The residue was converted into the (E)-2-butenedioate salt in 2-propanol. The salt was filtered off and crystallized from ethanol. The product was filtered off and dried, yielding 7.4 parts (85%) of 3-[2-[4-(1,2-benzisothiazol-3-yl)-1-piperazinyl]ethyl]-6,7,8,9-tetrahydro-2-methyl-4H-pyrido[1,2-a]pyrimidin-4-one (E)-2-butenedioate(1:1); mp. 186.0° C. (compound 1).

EXAMPLE 9

A mixture of 7.4 parts of 7-(2-bromoethyl)-3,4-dihydro-8-methyl-2H,6H-pyrimido-[2,1-b][1,3]thiazin-6-one monohydrobromide, 4.4 parts of 7-methyl-3-(1-piperazinyl)-1,2-benzisoxazole, 10 parts of sodium carbonate and 94 parts of N,N-dimethylformamide was stirred overnight at 90° C. After cooling, the reaction mixture was poured into water and the product was extracted with 4-methyl-2-pentanone. The extract was dried, filtered and evaporated. The residue was purified by column chromatography over silica gel using a mixture of trichloromethane and methanol (95:5 by volume) as eluent. The pure fractions were collected and the eluent was evaporated. The residue was crystallized from 4-methyl-2-pentanone. The product was filtered off and dried, yielding 3.8 parts (44.6%) of 3,4-dihydro-8-methyl-7-[2-[4-(7-methyl-1,2-benzisoxazol-3-yl)-1-piperazinyl]ethyl]-2H,6H-pyrimido[2,1-b][1,3]-thiazin-6-one; mp. 170.0° C. (compound 2).

EXAMPLE 10

A solution of 4.4 parts of 6-[2-[4-[(2,4-difluorophenyl)(hydroxyimino)methyl]-1-piperazinyl]ethyl]-2,3-dihydro-7-methyl-5H-thiazolo[3,2-a]pyrimidin-5-one in 45 parts of tetrahydrofuran was stirred at room temperature. 0.5 Parts of a sodium hydride dispersion 50% were added portionwise. Upon complete addition, 108 parts of methylbenzene were added and the reaction mixture was stirred for 18 hours at reflux temperature. After cooling, 16 parts of ethanol were added, followed by the addition of 3 parts of acetic acid. The whole was stirred for 10 minutes. The mixture was treated with ammonium hydroxide and the product was extracted with 4-methyl-2-pentanone. The extract was dried, filtered and evaporated. The residue was purified by column chromatography over silica gel using a mixture of trichloromethane and methanol (95:5 by volume) as eluent. The pure fractions were collected and the eluent was evaporated. The residue was crystallized from acetonitrile. The product was filtered off and dried, yielding 3.8 parts (91.4%) of 6-[2-[4-(6-fluoro-1,2-benzisoxazol-3-yl)-1-piperazinyl]-ethyl]-2,3-dihydro-7-methyl-5H-thiazolo[3,2-a]pyrimidin-5-one; mp. 193.0° C. (compound 3).

EXAMPLE 11

A mixture of 2.5 parts of 3-[2-[4-[(2-fluorophenyl)(2-phenylhydrazono)methyl]-1-piperazinyl]ethyl]-2-methyl-4H-pyrido[1,2-a]pyrimidin-4-one, 1 part of potassium carbonate and 27.8 parts of 1,2-ethanediol was stirred overnight at reflux temperature. The reaction mixture was cooled and then poured into water. The product was extracted with dichloromethane. The extract was dried, filtered and evaporated. The residue was purified by column chromatography over silica gel using a mixture of trichloromethane and methanol (95:5 by volume) as eluent. The pure fractions were collected and the eluent was evaporated. The residue was converted into the hydrochloride salt in 2-propanol. The salt was filtered off and dried, yielding 0.7 parts (25.5%) of 2-methyl-3-[2-[4-(1-phenyl-1H-indazol-3-yl)-1-piperazinyl]ethyl]-4H-pyrido[1,2-a]pyrimidin-4-one; mp. 260.0° C. (decomp.) (compound 4).

All compounds listed in Table 1 were prepared following methods of preparation described in examples 6 to 9, as is indicated in the column headed by Ex. No.

TABLE 1

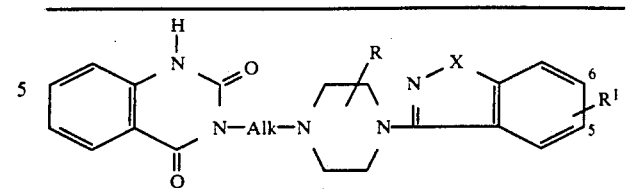

| Comp No. | Ex. No. | Alk | X | R¹ | Physical Data |
|---|---|---|---|---|---|
| 5 | 8 | —(CH$_2$)$_2$— | O | H | mp. 229.8° C. |
| 6 | 8 | —(CH$_2$)$_3$— | O | H | mp. 210.0° C. |
| 7 | 8 | —(CH$_2$)$_2$— | S | H | mp. 230.1° C. |
| 8 | 8 | —(CH$_2$)$_2$— | O | 5-Cl | HCl/mp. 264.0° C. |
| 9 | 8 | —(CH$_2$)$_2$— | NH | 6-F | mp. 276.7° C. |
| 10 | 8 | —(CH$_2$)$_2$— | NH | H | |

TABLE 2

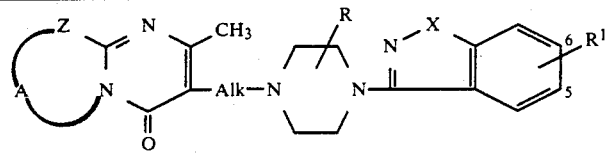

| Comp. No. | Ex. No. | —Z—A— | Alk | X | R¹ | Physical Data |
|---|---|---|---|---|---|---|
| 11 | 8 | —CH=CH—CH=CH— | —(CH$_2$)$_2$— | S | H | (E)-2-butenedioate (2:3)/mp. 202.9° C. |
| 12 | 8 | —CH=CH—CH=CH— | —(CH$_2$)$_2$— | O | 5-Cl | mp. 149.9° C. |
| 13 | 8 | —CH=CH—CH=CH— | —(CH$_2$)$_2$— | O | H | mp. 162.6° C. |
| 14 | 9 | —CH=CH—CH=CH— | —(CH$_2$)$_2$— | O | 7-CH$_3$ | mp. 154.6° C. |
| 15 | 10 | —CH=CH—CH=CH— | —(CH$_2$)$_2$— | O | 6-F | mp. 204.2° C. |
| 16 | 8 | —CH=CH—CH=CH— | —(CH$_2$)$_2$— | NH | 6-F | mp. 243.8° C. |
| 17 | 8 | —(CH$_2$)$_4$— | —(CH$_2$)$_2$— | O | H | mp. 152.2° C. |
| 18 | 8 | —(CH$_2$)$_4$— | —(CH$_2$)$_2$— | O | 5-Cl | (E)-2-butenedioate (1:1)/mp. 197.4° C. |
| 19 | 9 | —(CH$_2$)$_4$— | —(CH$_2$)$_2$— | O | 7-CH$_3$ | mp. 169.2° C. |
| 20 | 10 | —(CH$_2$)$_4$— | —(CH$_2$)$_2$— | O | 6-F | mp. 188.7° C. |
| 21 | 8 | —(CH$_2$)$_4$— | —(CH$_2$)$_2$— | NH | 6-F | mp. 249.5° C. |
| 22 | 8 | —S—(CH$_2$)$_3$— | —(CH$_2$)$_2$— | O | H | mp. 194.3° C. |
| 23 | 8 | —S—(CH$_2$)$_3$— | —(CH$_2$)$_2$— | O | 5-Cl | mp. 166.8° C. |
| 24 | 8 | —S—(CH$_2$)$_3$— | —(CH$_2$)$_2$— | S | H | mp. 162.8° C. |
| 25 | 10 | —S—(CH$_2$)$_3$— | —(CH$_2$)$_2$— | O | 6-F | mp. 210.1° C. |
| 26 | 8 | —S—(CH$_2$)$_2$— | —(CH$_2$)$_2$— | S | H | (E)-2-butenedioate (1:1)/mp. 223.8° C. |
| 27 | 8 | —S—(CH$_2$)$_2$— | —(CH$_2$)$_2$— | O | H | mp. 192.1° C. |
| 28 | 8 | —S—(CH$_2$)$_2$— | —(CH$_2$)$_2$— | O | 5-Cl | (E)-2-butenedioate (1:1)/mp. 185.7° C. |
| 29 | 8 | —S—(CH$_2$)$_2$— | —(CH$_2$)$_2$— | NH | 6-F | mp. 264.6° C. |
| 30 | 8 | —S—CH=CH— | —(CH$_2$)$_2$— | S | H | (E)-2-butenedioate (1:1)/mp. 232.7° C. |
| 31 | 8 | —S—CH=CH— | —(CH$_2$)$_2$— | O | H | mp. 210.8° C. |
| 32 | 8 | —S—CH=CH— | —(CH$_2$)$_2$— | O | 5-Cl | mp. 120.4° C. |
| 33 | 9 | —S—CH=CH— | —(CH$_2$)$_2$— | O | 7-CH$_3$ | mp. 149.6° C. |
| 34 | 10 | —S—CH=CH— | —(CH$_2$)$_2$— | O | 6-F | mp. 217.0° C. |
| 35 | 8 | —S—CH=C(CH$_3$)— | —(CH$_2$)$_2$— | S | H | (E)-2-butenedioate (1:1)/mp. 233.1° C. |
| 36 | 8 | —S—CH=C(CH$_3$)— | —(CH$_2$)$_2$— | O | 5-Cl | mp. 163.9° C. |
| 37 | 8 | —S—CH=C(CH$_3$)— | —(CH$_2$)$_2$— | O | H | mp. 200.8° C. |
| 38 | 9 | —S—CH=C(CH$_3$)— | —(CH$_2$)$_2$— | O | 7-CH$_3$ | mp. 159.8° C. |
| 39 | 10 | —S—CH=C(CH$_3$)— | —(CH$_2$)$_2$— | O | 6-F | mp. 214.8° C. |
| 40 | 8 | —S—CH=C(CH$_3$)— | —(CH$_2$)$_2$— | NH | 6-F | mp. 266.9° C. |
| 41 | 8 | —CH=CH—CH=CH— | —(CH$_2$)$_2$— | NH | H | mp. 202.0° C. |
| 42 | 8 | —CH=CH—C(CH$_3$)=CH— | —(CH$_2$)$_2$— | O | H | mp. 150.2° C. |
| 43 | 8 | —CH=CH—C(CH$_3$)=CH— | —(CH$_2$)$_2$— | NH | 6-F | mp. 250.8° C. |
| 44 | 8 | —CH=CH—C(CH$_3$)=CH— | —(CH$_2$)$_2$— | NH | H | mp. 203.6° C. |
| 45 | 8 | —C(CH$_3$)=CH—CH=CH— | —(CH$_2$)$_2$— | O | H | mp. 169.7° C. |
| 46 | 8 | —C(CH$_3$)=CH—CH=CH— | —(CH$_2$)$_2$— | S | H | mp. 165.0° C. |
| 47 | 8 | —C(CH$_3$)=CH—CH=CH— | —(CH$_2$)$_2$— | NH | 6-F | mp. 228.8° C. |
| 48 | 8 | —CH=CH—CCl=CH— | —(CH$_2$)$_2$— | O | H | mp. 155.3° C. |
| 49 | 8 | —CH=CH—CCl=CH— | —(CH$_2$)$_2$— | NH | H | mp. 211.7° C. |
| 50 | 8 | —CH=CH—CBr=CH— | —(CH$_2$)$_2$— | O | H | mp. 167.4° C. |
| 51 | 8 | —CH=CH—CBr=CH— | —(CH$_2$)$_2$— | NH | 6-F | mp. 249.3° C. |
| 52 | 8 | —(CH$_2$)$_4$— | —(CH$_2$)$_2$— | NH | H | mp. 212.8° C. |
| 53 | 8 | —CH$_2$—CH(CH$_3$)—(CH$_2$)$_2$— | —(CH$_2$)$_2$— | NH | 6-F | mp. 272.8° C. |
| 54 | 8 | —CH(CH$_3$)—(CH$_2$)$_3$— | —(CH$_2$)$_2$— | O | H | mp. 157.8° C. |

TABLE 2-continued

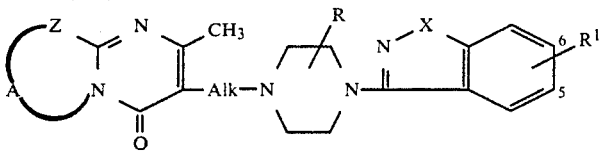

| Comp. No. | Ex. No. | —Z—A— | Alk | X | R¹ | Physical Data |
|---|---|---|---|---|---|---|
| 55 | 8 | —CH(CH₃)—(CH₂)₃— | —(CH₂)₂— | S | H | mp. 137.4° C. |
| 56 | 8 | —CH(CH₃)—(CH₂)₃— | —(CH₂)₂— | NH | 6-F | mp. 211.3° C. |
| 57 | 8 | —CH₂—C(CH₃)—CH₂—C(CH₃)— | —(CH₂)₂— | S | H | mp. 199.7° C. |
| 58 | 8 | —CHOH—(CH₂)₃— | —(CH₂)₂— | NH | H | mp. 222.3° C. |
| 59 | 8 | —CHOH—(CH₂)₃— | —(CH₂)₂— | S | H | mp. 220.9° C. |
| 60 | 8 | —S—(CH₂)₃— | —(CH₂)₂— | NH | 6-F | mp. 255.6° C. |
| 61 | 8 | —S—(CH₂)₃— | —(CH₂)₂— | NH | H | mp. 202.5° C. |
| 62 | 8 | —S—(CH₂)₂— | —(CH₂)₂— | NH | H | mp. 214.6° C. |
| 63 | 8 | —S—CH=CH— | —(CH₂)₂— | NH | 6-F | mp. >300° C. (dec.) |
| 64 | 8 | —S—CH=CH— | —(CH₂)₂— | NH | H | mp. 255.6° C. |
| 65 | 8 | —S—CH=C(CH₃)— | —(CH₂)₂— | NH | H | mp. 223.1° C. |
| 66 | 8 | —S—C(CH₃)=N— | —(CH₂)₂— | O | H | (E)-2-butenedioate (2:1)/mp. 236.6° C. |
| 67 | 8 | —S—C(CH₃)=N— | —(CH₂)₂— | NH | 6-F | mp. 284.3° C. |
| 68 | 8 | —CH=C(CH₃)—O— | —(CH₂)₂— | O | H | mp. 201.6° C. 0.5 H₂O |
| 69 | 8 | —CH=C(CH₃)—O— | —(CH₂)₂— | S | H | mp. 141.7° C. |
| 70 | 8 | —CH=C(CH₃)—O— | —(CH₂)₂— | NH | H | mp. 215.2° C. |
| 71 | 8 | —CH=C(CH₃)—O— | —(CH₂)₂— | NH | 6-F | mp. 229.4–229.9° C. |

(C) Pharmacological Examples

The activity of the subject compounds as antipsychotic agents is evidenced by the experimental data obtained in at least one of two different test procedures, viz., the combined apomorphine-, tryptamine- and norepinephrine tests in rats and the apomorphine test in dogs. The tests are carried out following the procedures described hereafter and the experimental data are summarized in table 3.

EXAMPLE 12

The Combined Apomorphine (APO)-, Tryptamine (TRY)- and Norepinephrine (NOR) Test in Rats The experimental animals used in this test were adult male Wistar rats (weight 240±10 g). After an overnight fast, the animals were treated subcutaneously or orally with an aqueous solution of the compound under investigation (1 ml/100 g body weight) (time=zero) and put in isolated observation cages. Thirty minutes thereafter (time=30 minutes) 1.25 mg/kg of apomorphine hydrochloride (APO) was injected intravenously and the rats were observed over a 1 hour period for the presence or absence of the following apomorphine-induced phenomena: agitation and stereotypic chewing. At the end of this 1 hour period (time=90 minutes) the same animals were injected intravenously with 40 mg/kg of tryptamine (TRY) and the presence of the typical tryptamine-induced bilateral tonic seizures and hyperaemia of the ears was noted. Two hours after pretreatment (time=120 minutes) finally, the same animals were challenged with 1.25 mg/kg intravenously of norepinephrine (NOR) and possible mortality was looked for up to 60 minutes later.

The table 3 gives the ED₅₀-values of a number of the compounds under consideration. As used herein, the ED₅₀-value represents the dose which protects 50% of the animals from apomorphine-, tryptamine- or norepinephrine-induced phenomena.

The Apomorphine Test in Dogs (APO-Dog)

The method used is described by P. A. J. Janssen and C. J. E. Niemegeers in Arzneim.-Forsch. (Drug Res.), 9, 765–767 (1959). The compounds listed in table 3 were administered subcutaneously or orally to beagle dogs at different doses and the animals were challenged one hour thereafter with a standard dose of 0.31 mg/kg (s.c.) of apomorphine.

The table 3 gives the ED₅₀-values of a number of the compounds under consideration. As used herein, the ED₅₀ value represents the dose which protects 50% of the animals from emesis.

The compounds listed in table 3 are not given for the purpose of limiting the invention thereto but only to exemplify the useful pharmacological activities of all the compounds within the scope of formula (I).

TABLE 3

| Comp. No. | Combined test in rats; ED₅₀ in mg/kg | | | | (APO)-dog test, ED₅₀ in mg/kg |
|---|---|---|---|---|---|
| | (APO) | (TRY)- convulsions | (TRY)- hyperaemia | (NOR) | |
| 3 | 0.02 | 0.005 | 0.00125 | 0.08 | 0.007 |
| 11 | 0.08 | 0.08 | 0.00031 | 1.25 | 0.45 |
| 15 | 0.04 | 0.08 | 0.005 | 0.31 | 0.015 |
| 16 | 0.08 | 0.08 | 0.005 | 0.08 | 0.0035 |
| 20 | 0.08 | 0.08 | 0.005 | 0.08 | 0.015 |
| 25 | 0.08 | 0.08 | ≦0.01 | 0.31 | 0.06 |
| 26 | 0.08 | 0.02 | 0.00125 | 5 | 0.03 |
| 27 | 0.03 | 0.03 | 0.00125 | 0.31 | 0.06 |
| 31 | 0.03 | 0.02 | 0.00031 | 1.25 | 0.03 |
| 34 | 0.02 | 0.08 | <0.01 | 0.31 | 0.015 |
| 39 | 0.08 | 0.04 | <0.04 | 0.31 | 0.03 |
| 40 | 0.02 | 0.02 | 0.00031 | 0.08 | 0.0025 |
| 41 | 0.08 | 0.04 | 0.005 | 1.25 | 0.03 |
| 45 | 0.04 | 0.08 | 0.02 | 1.25 | >0.01 |
| 47 | 0.04 | 0.08 | 0.000125 | 0.08 | 0.001 |
| 55 | 0.04 | 0.04 | 0.0025 | 10 | >0.01 |
| 56 | 0.08 | 0.08 | 0.005 | 0.16 | 0.0045 |
| 63 | 0.02 | 0.02 | 0.00125 | 0.16 | 0.001 |
| 64 | 0.08 | 0.08 | 0.005 | 1.25 | 0.0035 |
| 65 | 0.08 | 0.04 | 0.00063 | 1.25 | 0.0035 |

(D) Composition Examples

The following formulations exemplify typical pharmaceutical compositions in dosage unit form suitable for systemic administration to animal and human subjects in accordance with the present invention. "Active ingredient" (A.I.) as used throughout these examples relates to a compound of formula (I) or a pharmaceutically acceptable acid addition salt thereof.

EXAMPLE 13

Oral Drops

500 Parts of the A.I. was dissolved in 0.5 l of 2-hydroxypropanoic acid and 1.5 l of the polyethylene glycol at 60°~80° C. After cooling to 30°~40° C. there were added 35 l of polyethylene glycol and the mixture was stirred well. Then there was added a solution of 1750 parts of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

EXAMPLE 14

Oral Solution

9 Parts of methyl 4-hydroxybenzoate and 1 part of propyl 4-hydroxybenzoate were dissolved in 4 l of boiling purified water. In 3 l of this solution were dissolved first 10 parts of 2,3-dihydroxybutanedioic acid and thereafter 20 parts of the A.I. The latter solution was combined with the remaining part of the former solution and 12 l 1,2,3-propanetriol and 3 l of sorbitol 70% solution were added thereto. 40 Parts of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the A.I. per teaspoonful (5 ml). The resulting solution was filled in suitable containers.

EXAMPLE 15

Capsules

20 Parts of the A.I., 6 parts sodium lauryl sulfate, 56 parts starch, 56 parts lactose, 0.8 parts colloidal silicon dioxide, and 1.2 parts magnesium stearate were vigorously stirred together. The resulting mixture was subsequently filled into 1000 suitable hardened gelatin capsules, each comprising 20 mg of the A.I.

EXAMPLE 16

Film-Coated Tablets

Preparation of tablet core
A mixture of 100 parts of the A.I., 570 parts lactose and 200 parts starch was mixed well and thereafter humidified with a solution of 5 parts sodium dodecyl sulfate and 10 parts polyvinylpyrrolidone (Kollidon-K 90 ®) in about 200 ml of water. The wet powder mixture was sieved, dried and sieved again. Then there was added 100 parts microcrystalline cellulose (Avicel ®) and 15 parts hydrogenated vegetable oil (Sterotex ®). The whole was mixed well and compressed into tablets, giving 10.000 tablets, each containing 10 mg of the A.I.
Coating To a solution of 10 parts methyl cellulose (Methocel 60 HG ®) in 75 ml of denaturated ethanol there was added a solution of 5 parts of ethyl cellulose (Ethocel 22 cps ®) in 150 ml of dichloromethane. Then there were added 75 ml of dichloromethane and 2.5 ml 1,2,3-propanetriol. 10 Parts of polyethylene glycol was molten and dissolved in 75 ml of dichloromethane. The latter solution was added to the former and then there were added 2.5 parts of magnesium octadecanoate, 5 parts of polyvinylpyrrolidone and 30 ml of concentrated colour suspension (Opaspray K-1-2109 ®) and the whole was homogenated. The tablet cores were coated with the thus obtained mixture in a coating apparatus.

EXAMPLE 17

Injectable Solution 1.8 Parts methyl 4-hydroxybenzoate and 0.2 parts propyl 4-hydroxybenzoate were dissolved in about 0.5 l of boiling water for injection. After cooling to about 50° C. there were added while stirring 4 parts lactic acid, 0.05 parts propylene glycol and 4 parts of the A.I. The solution was cooled to room temperature and supplemented with water for injection q.s. ad 1 l, giving a solution comprising 4 mg/ml of A.I. The solution was sterilized by filtration (U.S.P. XVII p. 811) and filled in sterile containers.

EXAMPLE 18

Suppositories

3 Parts A.I. was dissolved in a solution of 3 parts 2,3-dihydroxybutanedioic acid in 25 ml polyethylene glycol 400. 12 Parts surfactant (SPAN ®) and triglycerides (Witepsol 555 ®) q.s. ad 300 parts were molten together. The latter mixture was mixed well with the former solution. The thus obtained mixture was poured into moulds at a temperature of 37°–38° C. to form 100 suppositories each containing 30 mg/ml of the A.I.

What is claimed is:
1. A chemical compound having the formula

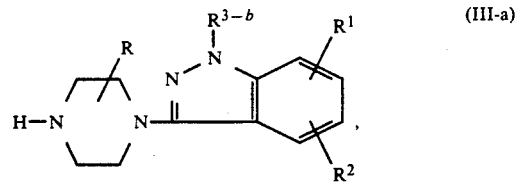

a pharmaceutically acceptable acid addition salt form thereof or a stereochemically isomeric form thereof, wherein:
R is hydrogen or $C_{1-6}$alkyl;
$R^1$ and $R^2$ each independently are hydrogen, halo, hydroxy, $C_{1-6}$alkyloxy or $C_{1-6}$alkyl;
$R^{3-b}$ is hydrogen, $C_{1-6}$alkyl or aryl$C_{1-6}$alkyl.
2. A compound according to claim 1 wherein:
R represents hydrogen;
$R^1$ represents hydrogen or halo;
$R^2$ represents hydrogen; and
$R^{3-b}$ represents hydrogen.
3. A compound according to claim 2 wherein the compound is 6-fluoro-3-(1-piperazinyl)-1H-indazole or 3-(1-piperazinyl)-1H-indazole.

* * * * *